May 1, 1973 D. L. ARMSTRONG Plant Pat. 3,322
ROSE PLANT
Filed April 15. 1971
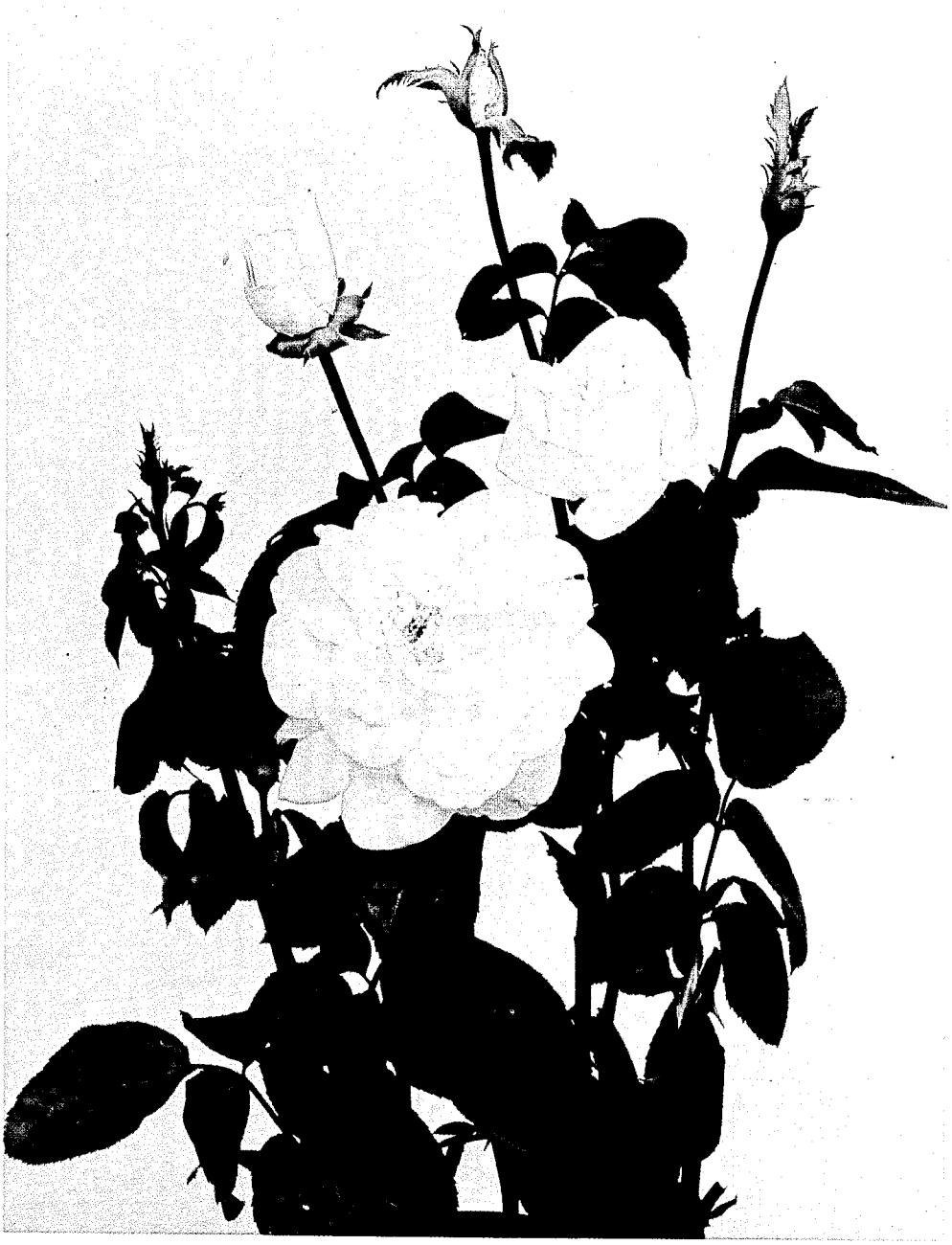

United States Patent Office

Plant Pat. 3,322
Patented May 1, 1973

3,322
ROSE PLANT
David L. Armstrong, Upland, Calif., assignor to Armstrong Nurseries, Inc., Ontario, Calif.
Filed Apr. 15, 1971, Ser. No. 134,517
Int. Cl. A01h 5/00
U.S. Cl. Plt.—15 1 Claim

ABSTRACT OF THE DISCLOSURE

A hybrid tea rose plant which bears large yellow blooms on long, strong stems. Most stems bear a single bloom, though some may bear three or four in an irregular cluster. The flower may span as much as 5½ inches when fully opened, and may contain as many as forty petals. The plant blooms freely outdoors almost continuously during the growing season. The general effect of the newly-opened flower is almost pure rich yellow, with little if any other coloration.

The invention relates to a new class of hybrid tea rose. The plant is a seedling of the tall bushy outdoor type, cultivated for cut flowers primarily and for garden decoration. It was propagated by David L. Armstrong in Ontario, Calif., having as its seed parent "High Time" and, as its pollen parent, "Imperial Gold." It holds its distinguishing characteristics through succeeding propagations by budding.

The new variety bears its flowers usually singly on strong long stems. Sometimes three or four blooms may be carried on one stem, however, in an irregular cluster. The plant blooms freely outdoors, and almost continuously during the growing season. It has a moderate tea to spicy fragrance.

This new variety of rose plant differs from its seed parent, High Time, in the following particulars:

The color of the new variety is predominantly brilliant yellow, both in the bud and in the opening flower, but sometimes displays a slightly greenish hue. The seed parent, in contrast, is of claret-rose color, with reverse of gold and pink.

The fragrance of the new variety is a moderate tea to spicy odor; the seed parent, on the other hand, is very fragrant, of a spicy odor.

The flowers of the new variety have from 35 to 40 petals arranged about 5 to 15 petaloids, whereas the flowers of its seed parent typically had 18 to 28 petals.

The habit of growth is more vigorous with the new variety than with High Time, even though High Time should itself be rated as a very vigorous grower.

The peduncles of the new variety are characteristically smooth, except for a few scattered glands, whereas the peduncles of High Time are typically covered with numerous small prickles and stipitate glands of varied sizes.

The new variety is distinct from its pollen parent, Imperial Gold, in the following particulars:

The habit of growth of the new variety is substantially more erect than that of Imperial Gold, which is substantially more spreading, even though it is not extreme in its spreading habit.

The color of the petaloids in the new variety is more or less uniformly yellow, whereas in the flowers of the pollen parent the petaloids are strongly marked with scarlet or near crimson on many individual petaloids.

The flowers of the new variety range from 4½ to 5½ inches, whereas those of Imperial Gold are generally smaller, ranging from 3½ to 4½ inches. Furthermore, the flowers of the new variety, as previously noted, contain from 35 to 40 petals with 5 to 15 petaloids, whereas the flowers of the pollen parent have only 30 to 35 petals.

The flower-bearing stems of the new variety are very long, whereas those of the pollen parent are shorter even though sturdier.

The new variety rarely sets hips, whereas the pollen parent, Imperial Gold, sets hips rather freely under garden conditions.

The internodes on this view variety are substantially longer than those of Imperial Gold.

The accompanying drawing illustrates the plant in color and shows the flowering thereof from bud to full bloom.

Throughout this specification, color names beginning with a small letter signify that the name of that color, as used in common speech, is aptly descriptive. Color names beginning with a capital letter designate values based upon the Nickerson Color Fan, put out by Munsell Color Co.

*Bud*

The peduncle is long and of heavy caliper, being erect and usually smooth. The color is near Strong Yellow Green, 5GY 6/8, overlaid with near Moderate Yellow Green, 2.5GY 5/5, in areas exposed to the sun.

Before the calyx breaks, the bud is medium to large in size, of medium to long length, is pointed and ovoid in form.

As the calyx breaks, the color is between Brilliant Greenish Yellow, 7.5Y 9/8, and Brilliant Yellow, 5Y 9/9. The inner surface of the sepals carries a fine, woolly tomentum.

The margins of alternate sepals are lined with a fine woolly tomentum; margins of others with several to many small stipitate glands and small slender foliaceous parts.

The outside surface of the sepals is usually smooth.

The sepals are usually with foliaceous appendages extending to one-half or more of sepal length.

As the first petal opens, it is average to large in size, of medium length, ovoid, and usually urn-shaped. The color on the outside of the petal is near Brilliant Yellow, 2.5Y 9/9. The inside surface of the petal shows near Brilliant Yellow, 5Y 9/9, blending with near Vivid Yellow, 5Y 8/12 toward the base of the petal. The bud opens up well and is not retarded or prevented from opening by cold, hot, wet or dry weather.

*Bloom*

The size of the bloom when fully open is average to large, ranging from 4½ to 5½ inches. The petalage is double, with from 35 to 40 petals arranged regularly plus 5 to 15 petaloids. The bloom is high centered at first, becoming cupped to high centered.

At first the petals are tightly cupped, with tips reflexed outward, becoming later at maturity loosely flat to cupped, with tips reflexed outward.

Outside and intermediate petals of the newly opened flower are usually reflexed outward, both along the apex and the edges. All petals on a three-days open flower are usually reflexed slightly outward, both along the apex and the edges.

The petals are of medium thickness, and are satiny in texture, both inside and outside. The outside petals are broadly obovate, with apex flat, and sometimes with 1 to 2 notches. The intermediate petals are also obovate, but with apex rounded, and sometimes with 1 or 2 notches. The inside petals also are obovate, with apex rounded. The colors may be modified by being shaded and/or washed with other colors.

The paragraphs immediately following describe color values observed in a flower newly opened in the month of September. The plant had been grown outdoors, in Ontario, Calif.

The outer surface of the outside petal is near Brilliant Yellow, 2.5Y 9/9, blending with near Brilliant Greenish Yellow, 7.5Y 9/8 toward the base of the petal. The inner surface of the outside petal is near Brilliant Yellow, 5Y 9/9, blending with near Brilliant Greenish Yellow, 7.5Y 9/8 toward the base of the petal.

The outer surface of the intermediate petal is near Brilliant Yellow, 2.5Y 9/9, blending with near Brilliant Greenish Yellow, 7.5Y 9/8, toward the base of the petal. The inner surface of the intermediate petal is near Brilliant Yellow, 5Y 9/9, blending with near Vivid Greenish Yellow, 7.5Y 8/12, toward the base of the petal.

The outer surface of the inner petal is near Brilliant Yellow, 5Y 9/9. The inner surface of the inner petal is near Brilliant Yellow, 5Y 9/9, blending with near Vivid Yellow, 5Y 8/12, toward the base of the petal.

The paragraphs immediately following describe the color values observed in a bloom which had been open for three days, outdoors, in the month of September. The plant had been grown outdoors, in Ontario, Calif.

The outer surface of the outside petal was between Brilliant Yellow, 5Y 9/9, and Brilliant Greenish Yellow, 7.5Y 9/8. The same color values characterized the inner surface of the outside petal.

The outer surface of the inside petal was between Brilliant Yellow, 5Y 9/9, and Brilliant Greenish Yellow, 7.5Y 9/8. The same color values characterized the inner surface of the inside petal.

The general color effect of the newly opened flower is between Vivid Yellow, 2.5Y 8/12, and Brilliant Yellow, 5Y 9/9. The bloom after being three days open gives a general color effect which is between Brilliant Yellow, 5Y 9/9, and Brilliant Greenish Yellow, 7.5Y 9/8. The petals drop off cleanly and are not particularly affected in this respect by cold, hot, wet, or dry weather.

The flower on the bush in the garden persists for from 3 to 4 days in the month of August, in the locality named. Cut roses grown outdoors and kept at living-room temperatures will last from 2 to 3 days in the month of August.

*Reproductive organs*

Stamens: The stamens are average in number, regularly arranged about the pistils, a few of them being mixed with petaloids.

Filaments: The filaments are medium length to long, being 5 to 15 mm. in length, and near Vivid Greenish Yellow, 7.5Y 8/12, in color. Most are with anthers.

Anthers: The anthers are of medium size, all opening approximately at once. On both the upper and lower side the margins are near Strong Orange Yellow, 10YR 7/10, and the central area is near Brilliant Greenish Yellow, 7.5Y 9/8.

Pollen: The pollen is moderately abundant, near Moderate Orange Yellow, 10YR 8/10, in color.

Pistils: The pistils are approximately 75 in number, this being average.

Styles: The styles are uneven, average to long in length, thin caliper, and bunched. The upper one-third of the style is near Dark Red, 2.5R 3/7; the remainder near Brilliant Greenish Yellow, 7.5Y 9/8.

Stigma: The stigma is near Moderate Orange Yellow, 7.5YR 8/8, in color.

Ovaries: The ovaries usually are all enclosed in the calyx.

Hips: No hips were observed on plants grown at Ontario, Calif.

Sepals: The sepals are permanent. They are of medium length and spear-shaped. The color, both inside and outside, was not significant.

Seeds: The new variety is highly sterile, and no seed was produced.

*Foliage*

The compound leaves usually comprise three to seven leaflets. They are abundant, large, leathery and semi-glossy in texture. The leaflets are broadly oval, with apex acute, base round, and margin simply serrate.

The mature foliage displays upon its upper surface a near Moderate Olive Green, 5GY 4/3. The under surface is Moderate Yellow Green, 7.5GY 5/7.

The young foliage on its upper surface is near Moderate Olive, 10Y 4/3; on its under surface it is near Light Olive, 7.5Y 5/5.

The rachis is average to heavy in size, grooved on the upper side, with a few stipitate glands on the edges. The under side is smooth, with few if any small prickles.

The stipules are medium-length, with short points turning out at an angle of more than 45°.

The plant displays a more than average resistance to mildew, when compared with other varieties now in commerce under comparable conditions, when grown at Ontario, Calif.

*Growth*

The plant is of upright-spreading habit, much branched. It displays a very vigorous growth. The canes are of heavy caliper.

The main stems are near Moderate Yellow Green, 5GY 5/6, in color. They bear several large prickles which are medium-length, hooked slightly downward, with short to medium-length narrow base. Their color is near Strong Yellowish Brown, 10YR 5/6. There are few small prickles, and their color is the same as that of the large prickles. There are no hairs.

The branches are a color between Moderate Yellow Green, 7.5GY 5/7, and Moderate Yellow Green, 5GY 5/6. They carry several large prickles which are medium-length, hooked slightly downward, with medium-length, narrow base. Their color is near Strong Greenish Yellow, 7.5Y 7/9. There are a few small prickles and their color is the same as that of the large prickles. There are no hairs.

New shoots have a color near Moderate Yellow Green, 5GY 5/6. There are a few large prickles, short to medium-length, hooked slightly downward, with medium-length narrow base. Their color is near Dark Yellow, 5Y 6/7. There are a few small prickles, and their color is the same as that of the large prickles. There are no hairs.

I claim:

1. The new and distinct variety of hybrid tea rose plant, substantially as herein illustrated and described, which is characterized by a combination of two or more of the following features, namely: its extremely vigorous and upright habit of growth; the abundance of its foliage, comprising large, semi-glossy leaves; its unusually long stems with smooth peduncles, most of such stems carrying a single bloom, but some carrying up to four blooms in an irregular cluster; the size of its blooms varying from average to large, and their color, being an over-all effect of brilliant yellow or slightly greenish yellow.

No references cited.

ROBERT E. BAGWILL, Primary Examiner